United States Patent
Bodor et al.

[11] 3,939,253
[45] Feb. 17, 1976

[54] NOVEL, TRANSIENT PRO-DRUG FORMS OF L-DOPA USEFUL IN THE TREATMENT OF PARKINSON'S DISEASE

[75] Inventors: Nicolae S. Bodor; Kenneth B. Sloan; Anwar A. Hussain, all of Lawrence, Kans.

[73] Assignee: Interx Research Corporation, Lawrence, Kans.

[22] Filed: Apr. 10, 1975

[21] Appl. No.: 566,748

Related U.S. Application Data

[62] Division of Ser. No. 412,419, Nov. 2, 1973, Pat. No. 3,891,696.

[52] U.S. Cl. .............................. 424/309; 424/319
[51] Int. Cl.[2] ................ A61K 31/24; A61K 31/195
[58] Field of Search ................ 424/311, 319, 309

Primary Examiner—Stanley J. Friedman
Attorney, Agent, or Firm—Charles N. Blitzer

[57] ABSTRACT

There is provided, novel, transient pro-drug forms of L-DOPA (3,4-dihydroxy-L-phenylalanine), having the formula:

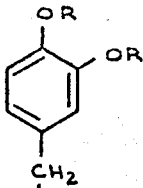

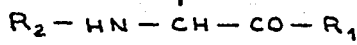

wherein R represents a member selected from the group consisting of a hydrogen atom, a —$COCH_3$ group, a —$COC_2H_5$ group, a —$COOC_2H_5$ group, and a —CO—$C(CH_3)_3$ group; wherein $R_1$ represents a member selected from the group consisting of a hydroxyl group, a —OM group (wherein M represents an alkali metal or an ammonium ion), a —$OCH_2$—$C_6H_5$ group, a —$OCH_3$ group, a —$OC_2H_5$ group, and —NH—CH($R_3$)COOH group, wherein $R_3$ represents the residue of any naturally occurring amino acid; and wherein $R_2$ represents a member selected from the group consisting of a hydrogen atom, a formyl group, a —CO—$C_6H_5$ group, a —CO—pyridyl group, a —CO($R_5$)—CH=CH($R_4$) group, and a $NH_2$—CH($R_6$)—CO— group, wherein $R_4$ represents a methyl group and wherein $R_5$ represents a member selected from the group consisting of a methyl group, a —$OC_2H_5$ group, and a $C_6H_5$— group, and wherein $R_6$ represents the residue of any naturally occurring amino acid, with the proviso that simultaneously, R cannot represent a hydrogen atom when $R_1$ represents a —$OCH_3$ group or a —OH group and when $R_2$ represents a hydrogen atom respectively;

R cannot represent a hydrogen atom when $R_1$ represents either a hydroxyl group or a —$OCH_3$ group and $R_2$ represents a —$COCH_3$ group, respectively;

R cannot represent a hydrogen atom when $R_1$ represents a hydroxyl group and $R_2$ represents a formyl group respectively, R cannot represent a hydrogen atom when $R_1$ represents a hydroxyl group and $R_2$ represents a benzoyl group, respectively; and, R cannot represent a hydrogen atom when $R_1$ represents a hydroxyl group and $R_6$ represents the residue of L-leucine, respectively.

These compounds are useful in the treatment of Parkinson's Disease.

15 Claims, No Drawings

NOVEL, TRANSIENT PRO-DRUG FORMS OF L-DOPA USEFUL IN THE TREATMENT OF PARKINSON'S DISEASE

This is a division of application Ser. No. 412,419, field Nov. 2, 1973, now U.S. Pat. No. 3,891,696.

BACKGROUND OF THE INVENTION

1. FIELD OF THE INVENTION

The present invention is directed to L-DOPA type compounds and more specifically, to certain novel, transient, pro-drug forms of L-DOPA, capable of administration to warm-blooded animals.

As employed in this application, the expression "pro-drug" denotes a derivative of a known and proven prior art compound, which derivative, when absorbed into the bloodstream of a warm-blooded animal, "cleaves" in such a manner as to release the proven drug form and permit the same to attain a higher bio-availability level than that which could be obtained if the proven drug form per se was administered.

Furthermore, as used in this application, the term "transient" denotes "cleavage" of the compounds of this invention in such a manner that the proven drug form is released and the remaining "cleaved" moiety is non-toxic and metabolized in such a manner that non-toxic, metabolic products are produced.

2. DESCRIPTION OF THE PRIOR ART

L-DOPA (3,4-dihydroxy-L-phenylalanine) is presently, generally accepted as the primary drug of choice in the treatment of Parkinson's Disease. However, due to its extensive extracerebral metabolism, extremely large doses (up to 8 grams) of this drug are required to initiate a medically acceptable therapeutic effect. Such large doses often cause intolerable side effects, such as gastro-intestinal symptoms (anorexia, nausea, and vomiting), orthostatic hypotension, and the development of involuntary movements. See, D. B. Calne, Clin. Pharmac. Ther., 11, 789 (1971). While decreasing the daily dose of L-DOPA would eliminate the above described side effects, nevertheless, Parkinsonism symptoms will return.

It has been known that a significant percentage of the amount of L-DOPA in contact with the gastric mucosa is metabolized (L. Rivera-Calimlim, C. A. Dujovane, J. P. Morgan, L. Lasagna, and J. R. Bianchine, Europ. J. Clin. Invest., 1, 313 (1971). This may delay and lower the attainable peaks of unchanged L-DOPA in the blood serum, which may be a critical factor for the passage of L-DOPA into the brain. Although, possibly, some metabolism of L-DOPA can occur in the human intestine, it would be expected to be minimal, because L-DOPA appears to be more rapidly absorbed in the intestine. On the other hand, L-DOPA, once delivered to the bloodstream by any suitable route (orally) is rapidly and continuously metabolized, since only 5.0 to 8.0 per cent of L-DOPA is protein bound. Consequently, L-DOPA is very susceptible to metabolic processes. See, H. Hinterberger, Biochem, Med., 5, 412 (1971).

The metabolism of L-DOPA can occur through a wide variety of metabolic pathways. The main initial steps are decarboxylation, 3-O-methylation, or transamination. L-DOPA appears to be metabolized within the brain in the same manner, as it is extracerebally metabolized. The necessary enzymes required to achieve these metabolisms, are DOPA-decarboxylase, COMT and MAO. These enzymes are well-known and widely distributed in man, including the liver, kidney, heart, and brain.

Due to the short half-life of L-DOPA in the blood stream (approximately 45 minutes) as determined by C. B. Coutinaho, H. E. Spiegel, et al, J. Pharm. Sci., 60, 1014 (1971) and B. Weiss, and G. V. Rossi, Biochem, Pharmacol., 12, 1399 (1963), and further due to its excessive metabolism prior to distribution in the bloodstream, a means of increasing L-DOPA blood levels without increasing L-DOPA dosage becomes exceedingly necessary.

The initial approach to this problem resides in decreasing the stomach elimination time, usually through the use of antacids, which appear to decrease gastric distress and result in somewhat higher L-DOPA blood levels. See, J. R. Bianchine, L. Rivera-Calimlim, C. A. Dujovene, J. P. Morgan, and L. Lasagna, Ann. N.Y. Acad. Sci., 179, 126 (1971).

In other instances, the employment of decarboxylase inhibitors appear to provide some improvement. For example, reference is made to the articles by A. Pletscher and C. Bartholini, Clin. Pharmac. Ther., 12, 344 (1971); D. L. Dunner, H. U. H. Brodie, and F. K. Goodwin, Ibid, 12, 212 (1971); and A. Barbeau, L. Gillo-Goffrey and H. Mars, Ibid, 12, 353 (1971).

With respect to the above, the most potent decarboxylase inhibitors are those of the hydrazine type, such as RO4-4602 [N-(D,L-Seryl)-N'-(2,3,4-trihydroxybenzyl)-hydrazine] and MK-486 (alpha-methyl-dopa-hydrazine). By employing these inhibitors, relatively small dosages of L-DOPA will provide therapeutic blood levels; however, the patient may be subjected to toxic effects as a result of such inhibitors.

It has also been found that the co-administration of COMT (catechol-O-methyl-transferase) inhibitors can also result in an increase in the free L-DOPA blood level. See, R. D. Robson, N. J. Antonaccio, and R. K. Reinhart, Europ. j. Pharmacol., 20, 104 (1972) and R. J. Valdessarini, and E. Greiner, Biochem. Pharmacol, 22, 247 (1973). With reference to these articles, it was determined that L-DOPA can severely tax normal methylation processes and therefore, interfere with methylation of biologically important substances. Moreover, it has also been determined that L-DOPA can increase blood concentrations of SAMe (s-adenosyl-methionine) in patients treated.

Therefore, it follows that blocking the methylation of L-DOPA might enhance bio-availability thereof, decrease the formation of methylated metabolites, and further prevent the occurrence of side effects associated with L-DOPA.

It has been demonstrated that the COMT inhibitors, do, indeed, aid in the reduction of the therapeutic dose required for L-DOPA. However, most of the available COMT inhibitors, including pyrogallol, desmethylpapaverine, tropolones, catecholacetamides, gallic acid esters, and substituted benzoates are of limited utility because of their lack of potency and duration of action, or in the alternative, simply due to their extreme toxicity.

SUMMARY OF THE INVENTION

It is one object of the present invention to provide novel, transient, pro-drug forms of L-DOPA, useful in the treatment of Parkinson's Disease in warm-blooded animals.

It is another object of the present invention to provide novel, transient, pro-drug forms of L-DOPA, which cleave in such a manner as to enable the original proven drug form (L-DOPA) to be released in the bloodstream of a warm-blooded animal and to further permit the cleaved moiety(ies), unassociated with the proven drug form to be non-toxic and metabolized in a non-toxic fashion.

Still, it is another object of the present invention to provide novel, transient, pro-drug forms of L-DOPA which, owing to their high solubility and/or better absorption properties, enable high blood levels of L-DOPA to be attained, following cleavage of the pro-drug form.

Finally, it is yet another object of the present invention to provide novel, transient, pro-drug forms of L-DOPA, which exhibit superior bio-availability over L-DOPA per se, when administered orally in a pharmaceutically acceptable oral dosage form. That is, applicants have concerned themselves with producing oral pro-drug forms of L-DOPA which would permit high blood levels of L-DOPA to be attained, but wherein the dose of the pro-drug form required to achieve a sufficient therapeutic effect is less than the therapeutic dose required of L-DOPA per se.

Accordingly, with the foregoing objects in mind, the present invention is directed to novel, transient, pro-drug forms of L-DOPA having the following formula:

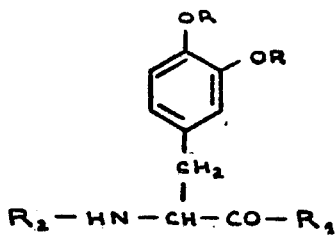

wherein R represents a member selected from the group consisting of a hydrogen atom, a —COCH$_3$ group, a —COC$_2$H$_5$ group, a —COOC$_2$H$_5$ group, and a —CO—C(CH$_3$)$_3$ group; wherein R$_1$ represents a member selected from the group consisting of a hydroxyl group, a —OM group (wherein M represents an alkali metal or an ammonium ion), a —OCH$_2$—C$_6$H$_5$ group, a —OCH$_3$ group, a —OC$_2$H$_5$ group, and a —N-H—CH(R$_3$)COOH group, wherein R$_3$ represents the residue of any naturally occurring amino acid; and wherein R$_2$ represents a member selected from the group consisting of a hydrogen atom, a formyl group, a —CO—C$_6$H$_5$ group, a —CO—pyridyl group, a —CO(R$_5$)—CH=CH(R$_4$) group and a NH$_2$—CH(R$_6$)—CO— group, wherein R$_4$ represents a methyl group and wherein R$_5$ represents a member selected from the group consisting of a methyl group, a —OC$_2$H$_5$ group, and a C$_6$H$_5$— group, and wherein R$_6$ represents the residue of any naturally occurring amino acid, with the proviso that simultaneously, R cannot represent a hydrogen atom when R$_1$ represents a —OCH$_3$ group or a —OH group and when R$_2$ represents a hydrogen atom, respectively;

R cannot represent a hydrogen atom when R$_1$ represents either a hydroxyl group or a —OCH$_3$ group and R$_2$ represents a —COCH$_3$ group, respectively;

R cannot represent a hydrogen atom when R$_1$ represents a hydroxyl group and R$_2$ represents a formyl group, respectively;

R cannot represent a hydrogen atom when R$_1$ represents a hydroxyl group and R$_2$ represents a benzoyl group, respectively; and, R cannot represent a hydrogen atom when R$_1$ represents a hydroxyl group and R$_6$ represents the residue of L-leucine, respectively, At this point in time, it is noteworthy to mention that applicants' approach to improving the oral bio-availability of L-DOPA differs from the approaches taken by the prior art to date. As applicants could determine, by partially inhibiting the main metabolic pathways of L-DOPA through the co-administration of decarboxylase inhibitors and/or COMT inhibitors, higher L-DOPA levels could be achieved using smaller therapeutic doses. However, applicants also observed that these approaches had their limitations and specifically, the toxicity of the enzymatic inhibitors employed at the necessary high dosage level required. Thus, while the use of such inhibitors might achieve the ultimate therapeutic result, the therapeutic dosage required of these inhibitors to achieve this result is so demanding that toxicity factors come into play.

Therefore, applicants' approach was to develop transient derivatives of L-DOPA which would exhibit a higher absorption rate (mainly due to their higher water and/or lipid solubility) and at the same time derivatives which would be less susceptible to extensive metabolism prior to and/or during the absorption process.

These derivatives were realized by placing protective groups on the reactive sites of the L-DOPA molecule; the catechol system, the amino and/or the carboxy group. Therefore, the transient derivatives of L-DOPA proposed herein can deliver L-DOPA at high blood levels after a chemical and/or enzymatic hydrolysis and yet, at a lesser dosage level than that required for L-DOPA per se. Moreover, once the derivatives of this invention are cleaved so as to release L-DOPA, the cleaved moiety(ies), other than the L-DOPA moiety will be metabolized into non-toxic products as a result of the protective groups placed on the reactive site of the L-DOPA molecule. Furthermore, the aforementioned cleaved moiety is non-toxic per se.

At this junction, it is interesting to further note that other individuals have suggested the use of possible pro-drug forms of L-DOPA, such as, the simple aliphatic esters thereof. However, they have reported only the D, L-DOPA esters. See, CH. M. Lai and W. D. Mason, *J. Pharm. Sci.*, 62, 511 (1973). In addition, the N-acetyl-L-DOPA esters have also been disclosed (see, Japanese Pat. Nos. 34,334/1972 and 34,335/1972), respectively. However, these compounds do not exhibit the properties observed with the compounds of this invention.

Among the compounds encompassed within the above generic formula, certain compounds are preferred. However, in any event, all compounds encompassed within the above generic formula meet applicants' criteria, as outlined earlier and are superior to L-DOPA per se in terms of solubility or absorption and/or bio-availability.

DETAILED DESCRIPTION OF THE INVENTION

The following compounds represent those compounds preferred among all compounds encompassed within the above described generic formula:

1. 3,4-diacetyloxy-L-phenylalanine and its HX salt, wherein X represents a pharmaceutically acceptable anion.

2. 3,4-diacetyloxy-N[1-methyl-2-acetylvinyl]-L-phenylalanine, and its alkali metal salt.

3. 3,4-diacetyloxy-L-phenylalanine-methyl ester and its HX salt, wherein X represents a pharmaceutically acceptable anion.
4. 3,4-dihydroxy-L-phenylalanine-benzyl ester and its HX salt, wherein X represents a pharmaceutically acceptable anion.
5. 3,4-diacetyloxy-L-phenylalanine-benzyl ester and its HX salt, wherein X represents a pharmaceutically acceptable anion.
6. Glycyl-3,4-diacetyloxy-L-phenylalanine and its HX salt, wherein X represents a pharmaceutically acceptable anion.
7. Glycyl-3,4-diacetyloxy-L-phenylalanine-methyl ester and its HX salt, wherein X represents a pharmaceutically acceptable anion.
8. 3,4-diacetyloxy-L-phenylalanyl-glycine and its HX salt, wherein X represents a pharmaceutically acceptable anion.
9. 3,4-dipropionyloxy-L-phenylalanine and its HX salt, wherein X represents a pharmaceutically acceptable anion.
10. 3,4-dipivalyloxy-L-phenylalanine and its HX salt, wherein X represents a pharmaceutically acceptable anion.
11. 3,4-dicarbethoxy-L-phenylalanine and its HX salt, wherein X represents a pharmaceutically acceptable anion.
12. 3,4-diacetyloxy-L-phenylalanine-ethyl ester and its HX salt, wherein X represents a pharmaceutically acceptable anion.
13. 3,4-dipivalyloxy-L-phenylalanine-ethyl ester and its HX salt, wherein X represents a pharmaceutically acceptable anion.
14. N-benzoyl-3,4-diacetyloxy-L-phenylalanine and its M salt, wherein M represents an alkali earth metal.
15. N-benzoyl-3,4-dipivalyloxy-L-phenylalanine and its M salt, wherein M represents an alkali metal.
16. N-formyl-3,4-diacetyloxy-L-phenylalanine and its M salt, wherein M represents an alkali metal.
17. N-formyl-3,4-dipivalyloxy-L-phenylalanine and its M salt, wherein M represents an alkali metal.
18. N-nicotinoyl-3,4-dihydroxy-L-phenylalanine and its M salt, wherein M represents an alkali metal.
19. Nicotinoyl-3,4-diacetyloxy-L-phenylalanine and its M salt, wherein M represents an alkali metal.
20. N-nicotinoyl-3,4-dipivalyloxy-L-phenylalanine and its M salt, wherein M represents an alkali metal.
21. 3,4-dihydroxy-N[1-methyl-2-acetylvinyl]-L-phenylalanine and its M salt, wherein M represents an alkali metal.
22. 3,4-dipivalyloxy-N[1-methyl-2-acetylvinyl]-L-phenylalanine and its M salt, wherein M represents an alkali metal.
23. 3,4-dihydroxy-N[1-ethoxy-2-acetylvinyl]-L-phenylalanine and its M salt, wherein M represents an alkali metal.
24. 3,4-diacetyloxy-N[1-ethoxy-2-acetylvinyl]-L-phenylalanine and its M salt, wherein M represents an alkali metal.
25. 3,4-dipivalyloxy-N[1ethoxy-2-acetylvinyl]-L-phenylalanine and its M salt, wherein M represents an alkali metal.
26. 3,4-dihydroxy-L-phenylalanyl-glycine and its HX salt, wherein X represents a pharmaceutically acceptable anion.
27. 3,4-dihydroxy-L-phenylalanyl-glycine-methyl ester and its HX salt, wherein X represents a pharmaceutically acceptable anion.
28. 3,4-dihydroxy-L-phenylalanyl-glycine-ethyl ester and its HX salt, wherein X represents a pharmaceutically acceptable anion.
29. 3,4-dihydroxy-L-phenylalanyl-glycine-benzyl ester and its HX salt, wherein X represents a pharmaceutically acceptable anion.
30. 3,4-diacetyloxy-L-phenylalanyl-glycine and its HX salt, wherein X represents a pharmaceutically acceptable anion.
31. 3,4-diacetyloxy-L-phenylalanyl-glycine-methyl ester and its HX salt, wherein X represents a pharmaceutically acceptable anion.
32. 3,4-diacetyloxy-L-phenylalanyl-glycine-ethyl ester and its HX salt, wherein X represents a pharmaceutically acceptable anion.
33. 3,4-diacetyloxy-L-phenylalanyl-glycine-benzyl ester and its HX salt, wherein X represents a pharmaceutically acceptable anion.
34. 3,4-dihydroxy-L-leucine and its HX salt, wherein X represents a pharmaceutically acceptable anion.
35. 3,4-dihydroxy-L-phenylalanyl-L-leucine-methyl ester and its HX salt, wherein X represents a pharmaceutically acceptable anion.
36. 3,4-dihydroxy-L-phenylalanyl-L-leucine-ethyl ester and its HX salt, wherein X represents a pharmaceutically acceptable anion.
37. 3,4-dihydroxy-L-phenylalanyl-L-leucine-benzyl ester and its HX salt, wherein X represents a pharmaceutically acceptable anion.
38. 3,4-diacetyloxy-L-phenylalanyl-L-leucine and its HX salt, wherein X represents a pharmaceutically acceptable anion.
39. 3,4-diacetyloxy-L-phenylalanyl-L-leucine-methyl ester and its HX salt, wherein X represents a pharmaceutically acceptable anion.
40. 3,4-diacetyloxy-L-phenylalanyl-L-leucine-ethyl ester and its HX salt, wherein X represents a pharmaceutically acceptable anion.
41. 3,4-diacetyloxy-L-phenylalanyl-L-leucine-benzyl ester and its HX salt, wherein X represents a pharmaceutically acceptable anion.
42. 3,4-dihydroxy-L-phenyalanyl-L-isoleucine and its HX salt, wherein X represents a pharmaceutically acceptable anion.
43. 3,4-dihydroxy-L-phenylalanyl-L-isoleucine-methyl ester and its HX salt, wherein X represents a pharmaceutically acceptable anion.
44. 3,4-dihydroxy-L-phenylalanyl-L-isoleucine-ethyl ester and its HX salt, wherein X represents a pharmaceutically acceptable anion.
45. 3,4-dihydroxy-L-phenylalanyl-L-isoleucine-benzyl ester and its HX salt, wherein X represents a pharmaceutically acceptable anion.
46. 3,4-diacetyloxy-L-phenylalanyl-L-isoleucine and its HX salt, wherein X represents a pharmaceutically acceptable anion.
47. 3,4-diacetyloxy-L-phenylalanyl-L-isoleucine-methyl ester and its HX salt, wherein X represents a pharmaceutically acceptable anion.
48. 3,4-diacetyloxy-L-phenylalanyl-L-isoleucine-ethyl ester and its HX salt, wherein X represents a pharmaceutically acceptable anion.
49. 3,4-diacetyloxy-L-phenylalanyl-L-isoleucine-benzyl ester and its HX salt, wherein X represents a pharmaceutically acceptable anion.
50. 3,4-dihydroxy-L-phenylalanyl-phenylalanine and its HX salt, wherein X represents a pharmaceutically acceptable anion.

51. 3,4-dihydroxy-L-phenylalanyl-phenylalanine-methyl ester and its HX salt, wherein X represents a pharmaceutically acceptable anion.
52. 3,4-dihydroxy-L-phenylalanyl-phenylalanine-ethyl ester and its HX salt, wherein X represents a pharmaceutically acceptable anion.
53. 3,4-dihydroxy-L-phenylalanyl-phenylalanine-benzyl ester and its HX salt, wherein X represents a pharmaceutically acceptable anion.
54. 3,4-diacetyloxy-L-phenylalanyl-phenylalanine and its HX salt, wherein X represents a pharmaceutically acceptable anion.
55. 3,4-diacetyloxy-L-phenylalanyl-phenylalanine-methyl ester and its HX salt, wherein X represents a pharmaceutically acceptable anion.
56. 3,4-diacetyloxy-L-phenylalanyl-phenylalanine-ethyl ester and its HX salt, wherein X represents a pharmaceutically acceptable anion.
57. 3,4-diacetyloxy-L-phenylalanyl-phenylalanine-benzyl ester and its HX salt, wherein X represents a pharmaceutically acceptable anion.
58. Glycyl-3,4-dihydroxy-L-phenylalanine and its HX salt, wherein X represents a pharmaceutically acceptable anion.
59. Glycyl-3,4-diacetyloxy-L-phenylalanine and its HX salt, wherein X represents a pharmaceutically acceptable anion.
60. Glycyl-3,4-dipivalyloxy-L-phenylalanine and its HX salt, wherein X represents a pharmaceutically acceptable anion.
61. Glycyl-3,4-dihydroxy-L-phenylalanine-methyl ester and its HX salt, wherein X represents a pharmaceutically acceptable anion.
62. Glycyl-3,4-dihydroxy-L-phenylalanine-ethyl ester and its HX salt, wherein X represents a pharmaceutically acceptable anion.
63. Glycyl-3,4-dihydroxy-L-phenylalanine-benzyl ester and its HX salt, wherein X represents a pharmaceutically acceptable anion.
64. Glycyl-3,4-diacetyloxy-L-phenylalanine-methyl ester and its HX salt, wherein X represents a pharmaceutically acceptable anion.
65. Glycyl-3,4-diacetyloxy-L-phenylalanine-ethyl ester and its HX salt, wherein X represents a pharmaceutically acceptable anion.
66. Glycyl-3,4-diacetyloxy-L-phenylalanine-benzyl ester and its HX salt, wherein X represents a pharmaceutically acceptable anion.
67. L-leucyl-3,4-diacetyloxy-L-phenylalanine and its HX salt, wherein X represents a pharmaceutically acceptable anion.
68. L-leucyl-3,4-dihydroxy-L-phenylalanine-methyl ester and its HX salt, wherein X represents a pharmaceutically acceptable anion.
69. L-leucyl-3,4-dihydroxy-L-phenylalanine-ethyl ester and its HX salt, wherein X represents a pharmaceutically acceptable anion.
70. L-leucyl-3,4-dihydroxy-L-phenylalanine-benzyl ester and its HX salt, wherein X represents a pharmaceutically acceptable anion.
71. L-leucyl-3,4-dihydroxy-L-phenylalanine-benzyl ester and its HX salt, wherein X represents a pharmaceutically acceptable anion.
72. L-leucyl-3,4-diacetyloxy-L-phenylalanine-methyl ester and its HX salt, wherein X represents a pharmaceutically acceptable anion.
73. L-leucyl-3,4-diacetyloxy-L-phenylalanine-ethyl ester and its HX salt, wherein X represents a pharmaceutically acceptable anion.
74. L-leucyl-3,4-diacetyloxy-L-phenylalanine-benzyl ester and its HX salt, wherein X represents a pharmaceutically acceptable anion.
75. L-isoleucyl-3,4-dihydroxy-L-phenylalanine and its HX salt, wherein X represents a pharmaceutically acceptable anion.
76. L-isoleucyl-3,4-diacetyloxy-L-phenylalanine and its HX salt, wherein X represents a pharmaceutically acceptable anion.
77. L-isoleucyl-3,4-dihydroxy-L-phenylalanine-methyl ester and its HX salt, wherein X represents a pharmaceutically acceptable anion.
78. L-isoleucyl-3,4-dihydroxy-L-phenylalanine-ethyl ester and its HX salt, wherein X represents a pharmaceutically acceptable anion.
79. L-isoleucyl-3,4-dihydroxy-L-phenylalanine-benzyl ester and its HX salt, wherein X represents a pharmaceutically acceptable anion.
80. L-isoleucyl-3,4-dihydroxy-L-phenylalanine-benzyl ester and its HX salt, wherein X represents a pharmaceutically acceptable anion.
81. L-isoleucyl-3,4-diacetyloxy-L-phenylalanine-methyl ester and its HX salt, wherein X represents a pharmaceutically acceptable anion.
82. L-isoleucyl-3,4-diacetyloxy-L-phenylalanine-ethyl ester and its HX salt, wherein X represents a pharmaceutically acceptable anion.
83. L-isoleucyl-3,4-diacetyloxy-L-phenylalanine-benzyl ester and its HX salt, wherein X represents a pharmaceutically acceptable anion.
84. Phenylalanyl-3,4-dihydroxy-L-phenylalanine and its HX salt, wherein X represents a pharmaceutically acceptable anion.
85. Phenylalanyl-3,4-diacetyloxy-L-phenylalanine and its HX salt, wherein X represents a pharmaceutically acceptable anion.
86. Phenylalanyl-3,4-dihydroxy-L-phenylalanine-methyl ester and its HX salt, wherein X represents a pharmaceutically acceptable anion.
87. Phenylalanyl-3,4-dihydroxy-L-phenylalanine-ethyl ester and its HX salt, wherein X represents a pharmaceutically acceptable anion.
88. Phenylalanyl-3,4-dihydroxy-L-phenylalanine-benzyl ester and its HX salt, wherein X represents a pharmaceutically acceptable anion.
89. Phenylalanyl-3,4-dihydroxy-L-phenylalanine-benzyl ester and its HX salt, wherein X represents a pharmaceutically acceptable anion.
90. Phenylalanyl-3,4-diacetyloxy-L-phenylalanine-methyl ester and its HX salt, wherein X represents a pharmaceutically acceptable anion.
91. Phenylalanyl-3,4-diacetyloxy-L-phenylalanine-ethyl ester and its HX salt, wherein X represents a pharmaceutically acceptable anion.
92. Phenylalanyl-3,4-diacetyloxy-L-phenylalanine-benzyl ester and its HX salt, wherein X represents a pharmaceutically acceptable anion.
93. 3,4-dihydroxy-L-phenylalanyl-3,4-dihydroxy-L-phenylalanine and its HX salt, wherein X represents a pharmaceutically acceptable anion.
94. 3,4-dihydroxy-L-phenylalanyl-3,4-dihydroxy-L-phenylalanine-methyl ester and its HX salt, wherein X represents a pharmaceutically acceptable anion.

95. 3,4-dihydroxy-L-phenylalanyl-3,4-dihydroxy-L-phenylalanine-ethyl ester and its HX salt, wherein X represents a pharmaceutically acceptable anion.
96. 3,4-dihydroxy-L-phenylalanyl-3,4-dihydroxy-L-phenylalanine-benzyl ester and its HX salt, wherein X represents a pharmaceutically acceptable anion.
97. 3,4-diacetyloxy-L-phenylalanyl-3,4-diacetyloxy-L-phenylalanine and its HX salt, wherein X represents a pharmaceutically acceptable anion.
98. 3,4-diacetyloxy-L-phenylalanyl-3,4-diacetyloxy-L-phenylalanine-methyl ester and its HX salt, wherein X represents a pharmaceutically acceptable anion.
99. 3,4-diacetyloxy-L-phenylalanyl-3,4-diacetyloxy-L-phenylalanine-ethyl ester and its HX salt, wherein X represents a pharmaceutically acceptable anion.
100. 3,4-diacetyloxy-L-phenylalanyl-3,4-diacetyloxy-L-phenylalanine-benzyl ester and its HX salt, wherein X represents a pharmaceutically acceptable anion.
101. Poly-3,4-dihydroxy-L-phenylalanine:

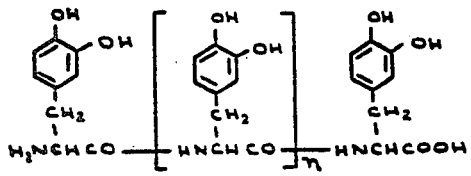

wherein n represents an integer of 1 or more.
102. Poly-3,4-diacetoxy-L-phenylalanine:

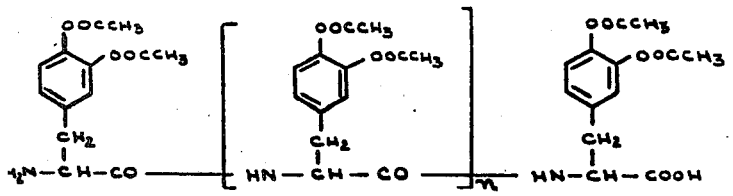

wherein n represents an integer of 1 or more.

The compounds encompassed within the above recited generic formula can be essentially grouped into eight classes, as described hereinafter. These will be referred to as classes (I) through (VIII).

THE COMPOUNDS OF CLASS (I):

The compounds of this particular class are those of the 3,4-diacylated-L-DOPA type and their HX salts, wherein X represents a conventional pharmaceutically acceptable acid addition salt anion, derived from a conventional pharmaceutically acceptable acid addition salt, such as a chloride ion, a bromide ion, a perchlorate ion, and the like. With respect to these compounds, R represents an acyl group; $R_1$ represents a hydroxy group; and $R_2$ represents a hydrogen atom.

THE COMPOUNDS OF CLASS (II):

The compounds of this class constitute the carboxy esters of L-DOPA and their respective HX salts, wherein X is defined as above. With respect to these compounds, R represents a hydrogen atom or an acyl group; $R_1$ represents a $-OCH_2-C_6H_5$ group, a $-OC_2H_5$ group, or a $-OCH_3$ group; and $R_2$ represents a hydrogen atom respectively; R cannot represent a hydrogen atom when $R_1$ represents either a hydroxyl group or a $-OCH_3$ group and when $R_2$ represents a $-COCH_3$ group respectively.

THE COMPOUNDS OF CLASS (III):

These compounds constitute the enamines derived from the compounds of class (I). With respect to these compounds, R represents a hydrogen atom or an acyl group; $R_1$ represents a hydroxyl group or a $-OM$ group, wherein M represents an alkali metal, such as sodium, potassium, etc., or an ammonium ion; and wherein $R_2$ represents a $-(R_5)CO-CH=CH(R_4)-$ group, wherein $R_4$ represents a methyl group and $R_5$ represents a member selected from the group consisting of a methyl group, a $C_6H_5$ group, or a $-OC_2H_5$ group.

THE COMPOUNDS OF CLASS (IV):

The compounds of this class constitute the amides derived from the compounds of class (I), wherein R represents an acyl group; $R_1$ represents a hydroxyl group or a $-OM$ group, wherein M has been defined previously, and $R_2$ represents a $-COH$ group, a $-CO-C_6H_5$ group, or a $-CO-$pyridyl group.

THE COMPOUNDS OF CLASS (V):

These compounds are the N-terminal dipeptides of L-DOPA wherein R represents a hydrogen atom or an acyl group; $R_2$ represents a hydrogen atom; and wherein $R_1$ represents a $-NHCH(R_3)COOH$ group, wherein $R_3$ represents the residue of a naturally occurring amino acid and the HX salt thereof, wherein X is defined as above.

THE COMPOUNDS OF CLASS (VI):

The compounds of this class constitute the C-terminal dipeptides of L-DOPA, wherein R represents a hydrogen atom or an acyl group; wherein $R_1$ represents a hydroxyl group, a $-OCH_3$ group, a $-OC_2H_5$ group, or a $-OCH_2-C_6H_5$ group; and wherein $R_2$ represents a $NH_2CH(R_6)CO$ group, wherein $R_6$ represents the residue of a naturally occurring amino acid and the HX salt thereof, wherein X is defined as above.

THE COMPOUNDS OF CLASS (VII):

The compounds of this class are those compounds of class (VI), which are basically dipeptides formed from two molecules of 3,4-dihydroxy-L-phenylalanine, wherein R represents a hydrogen atom or an acyl group, $R_1$ represents a hydroxyl group, a $-OCH_3$ group, a $-OC_2H_5$ group, or a $-OCH_2-C_6H_5$ group; $R_2$ represents a $NH_2-CH(R_6)-CO-$ group, and $R_6$ represents the residue of 3,4-dihydroxy-L-phenylalanine

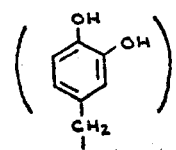

or 3,4-L-diacetyloxy-phenylalanine

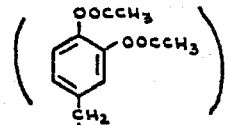

and the HX salts thereof, wherein X is defined as above.

THE COMPOUNDS OF CLASS (VIII):

The compounds of this class are those compounds encompassed within the above generic formula describing the compounds of this invention, and which have the following general formula:

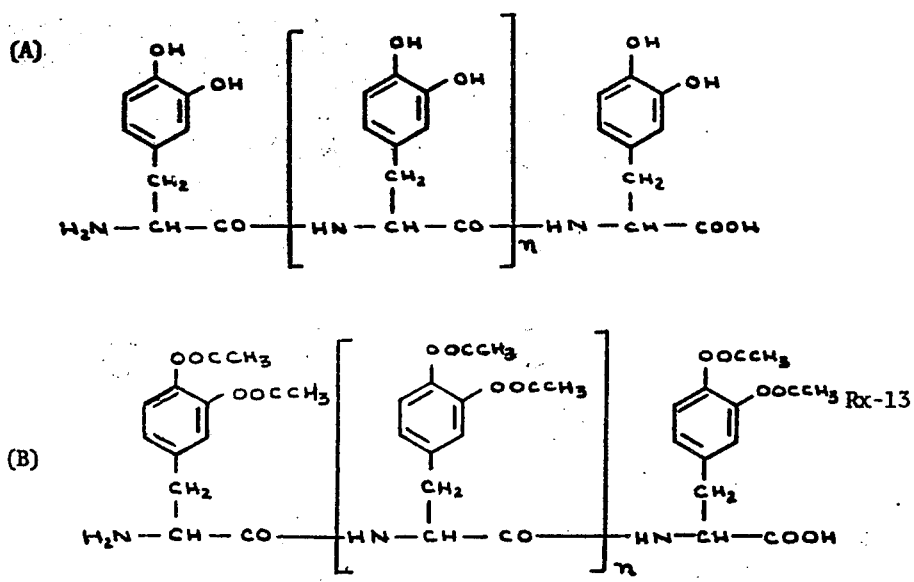

wherein n represents an integer of one or more and preferably, an integer within a range of from 7 to 20.

This class basically constitutes the polypeptides of L-DOPA per se, or its 3,4-diacetylated derivatives.

The compounds of classes (I) through (VIII) can be prepared by simple step-wise procedures as outlined below and as described in the various publications recited.

PREPARATION OF THE COMPOUNDS OF CLASS (I):

L-DOPA is reacted with a conventional acylating agent (e.g. acyl chloride or acyl anhydride) in the presence of a suitable solvent, (e.g., acetic acid, benzene, or a halohydrocarbon) in the presence of a strong mineral acid, such as hydrochloric acid, perchloric acid, etc., over a period of several hours (preferably, 2–6 hours) and over a temperature range of from 0° to 120°C, but preferably, at room temperature or that temperature which is equivalent to the boiling point of the solvent employed.

PREPARATION OF THE COMPOUNDS OF CLASS (II):

To prepare these compounds, L-DOPA is reacted with the corresponding alcohol in the presence of an acid catalyst (e.g. p-toluenesulfonic acid, benzenesulfonic acid, etc.), the water formed during the reaction being eliminated. The reaction is carried out at reflux temperatures and standard pressure until the theoretical amount of water is removed. See, L. Zervas, N. Winitz, and J. P. Greenstein, *J. Org. Chem.*, 22, 1515 (1957).

In one alternative method, L-DOPA can be reacted with the corresponding alcohol in the presence of hydrochloric acid, under anhydrous conditions, whereby the alcohol serves as the solvent per se. This reaction will occur at room temperature, though a temperature of from 40°–80°C is preferred. Standard pressure is employed and the reaction time will normally run between 7 and 24 hours.

In a second alternative method, L-DOPA can be reacted with the corresponding alcohol in the presence of thionyl chloride, whereby the alcohol will again serve as the solvent per se. In this reaction scheme, standard pressure is employed and the reaction temperature is approximately 0°C initially (during the addition of the reactants). Subsequently, the temperature will be raised to within a range of from 40° to 100°C. The reaction time required to carry out this particular reaction scheme will run, approximately, between 1 and 7 hours. See, M. Brenner and W. Huber, *Helv. Chim. Acta.*, 36, 1109 (1953); and R. P. Patel and S. Price, *J. Org. Chem.*, 30, 3575 (1965).

PREPARATION OF THE COMPOUNDS OF CLASS (III):

To prepare the compounds of this class, the beta, gamma-diketo derivative is reacted with L-DOPA in methanol or ethanol (solvent) in which an equivalent amount of MOH is introduced (M representing an alkali metal such as sodium or potassium or an ammonium ion) in a ratio of 1:1.1. The reaction is carried out over several hours at standard pressure and at a temperature ranging from room temperature to 60°C in the presence of a nitrogen atmosphere. Preferably, a reaction time of 24 hours is most suitable. See, J. A. Maclaren, *Aust. J. Chem.*, 25, 1293 (1972); E. Dane and T. Dockner, *Chem. Ber.*, 98, 789 (1964).

PREPARATION OF THE COMPOUNDS OF CLASS (IV):

These compounds are prepared by reacting L-DOPA with a conventional acylation agent, such as acyl chloride or acyl anhydride, or in the alternative, a conventional "mixed anhydride" system can be used. The reaction is carried out in a suitable solvent, such as an organic acid (acetic acid, propionic acid, etc.) at room temperature and standard pressure. In the alternative, the reaction can be carried out in a halohydrocarbon solvent at reflux temperatures in the presence of a tertiary amine. In either case, the reaction is carried out for a period ranging from 1 to 6 hours. See, J. C. Sheehan and D-D. H. Yang, *J. Amer. Chem. Soc.*, 80, 1154 (1958).

PREPARATION OF THE COMPOUNDS OF CLASS (VI):

The preparation of the compounds of this class is discussed prior to the preparation of the compounds of class (V) as a matter of convenience.

The preparation of the compounds of class (VI) is in accordance with conventional dipeptide synthesis procedures. In the first step, acylation of the catechol hydroxyl groups is carried out in accordance with the acylation scheme described above, for preparing the compounds of class (I). Secondly, the carboxyl group of L-DOPA is esterified in accordance with the esterification procedure outlined for the preparation of the compounds of class (II) above. In the third step, the L-DOPA molecule is coupled with a suitable N-protected natural amino acid by known procedures (e.g., dicyclohexylcarbodiimide in tetrahydrofuran and/or a halohydrocarbon). This reaction is carried out at room temperature over a period of time ranging from 3 to 24 hours; however, as an alternative, the "mixed anhydride" method can be employed at a temperature of 0°C initially (for 0.5 to 1.0 hours) and then, at a temperature approximating room temperature for a period of time of from 2 to 6 hours. The "mixed anhydride" can, without limitation, be a mixture with pivaloyl chloride or pivaloyl chlorocarbonate.

At this point, it is important to mention that steps (1) through (3), heretofore described, need not necessarily be carried out in sequential order; that is, the sequence can vary with the priviso that steps (1) or (2) proceed step (3).

Illustrative of N-protective groups for the amino acid which can be employed in step (3), are the carbobenzoxy group and the formyl group.

In step (4), cleavage of the N-protective group is achieved in a conventional manner. As an example, when the N-protective group is a carbobenzoxy group, catalytic hydrogenation is employed over a catalyst comprising palladium on carbon (5–10%), in methanol or ethanol or any other suitable solvent. The reaction is carried out at standard pressure, room temperature, and for a period of time approximating several hours. When the N-protective group is a formyl group, its cleavage can be carried out by various procedures, and preferentially, in a mixture of methanol and hydrochloric acid. The reaction is normally carried out at standard pressure and room temperature over a period of time ranging from 2 to 4 days.

In step (5), cleavage of the carboxy ester ($R_1$) is achieved. For instance, if $R_1$ is a —$CH_2$—$C_6H_5$ group, catalytic hydrogenation is carried out over a catalyst of palladium on carbon (5–10%) in methanol or ethanol, at standard pressure at room temperature. On the other hand, if $R_1$ represents an —$OCH_3$ group, an alkaline hydrolysis is employed (sodium hydroxide, sodium bicarbonate, barium hydroxide, etc.) in the presence of alcohol, methanol or ethanol under a nitrogen atomsphere, at room temperature, for a period approximating several hours.

In step (6) cleavage of the catechol protective system is achieved. For instance, if the catechol protective group is an acyl group, alkaline or acid hydrolysis is introduced, and if the catechol protective group is a benzyl group, catalytic hydrogenation as described above is employed.

Finally, in step (7), arbitrary adjustments in the isolated L-DOPA derivative can be made, such as salt formation (if the reaction did not directly provide the salt) and reacylation of the catechol system. Such procedures are known and understood by the skilled artisan concerned with the subject matter of this invention.

PREPARATION OF THE COMPOUNDS OF CLASS (V):

These compounds are prepared in a manner similar to that employed to prepare the compounds of class (VI). Step (1) of this precedure is identical to step (1) of the procedure employed to prepare the compounds of class (VI). In step (2), protection of the amino group is achieved through the use of conventional protective groups, and preferably, the formyl group. For instance, the N-formyl derivative can be prepared by the "mixed" acetic-formic anhydride method, in acetic acid, by first cooling the reaction mixture below room temperature and then raising the temperature of the reaction mixture to room temperature for approximately 1 hour. In step (3), coupling with a suitable natural amino acid ester is carried out in the manner prescribed in step (3) for the preparatory procedure described for preparing the compounds of class (VI). In step (4), cleavage of the carboxy ester is achieved. For instance, if the carboxy ester is a benzyl ester, catalytic hydrogenation is carried out over a palladium on carbon (5–10%) catalyst as illustrated in step (4) respective of the preparatory procedure for preparing the compounds of class (VI). On the other hand, if the carboxy ester is a methyl or ethyl ester, alkaline hydrolysis is employed in accordance with the method described in step (5) of the preparatory scheme for preparing the compounds of class (VI). In step (5), cleavage of the N-protective group is carried out in accordance with step (4) of the preparatory procedure for obtaining the compounds of class (VI), the procedure varying depending upon whether the N-protective group is a carbobenzoxy group, a formyl group, or any other suitable protective group. Steps (6) and (7) respectively, are identical to steps (6) and (7) described above in the preparatory scheme for preparing the compounds of class (VI).

The skilled artisan concerned with the subject matter of this invention can readily appreciate that steps (4) through (6) can occur simultaneously in accordance with the above recited conditions. Moreover, with respect to the preparation of the compounds of class (VI), in addition to the fact that steps (1) and (2) can be varied in sequence, provided they precede step (3), steps (4) through (6) can also be varied with the proviso that they follow step (3).

Few dipeptides containing C- or N- terminal D, L-DOPA have been reported in the literature, such as, D, L-3,4-dihydroxyphenylalanyl-glycine, -D, L-alanine, -D, L-leucine, -D, L-phenylalanine, -D, L-tyrosine, using phthaloyl -D, L-3,4-dihydroxyphenylalanine, since it was concluded that the amino group in D, L-DOPA cannot be protected with carbobenzoxy or p-nitrocarbobenzoxy groups. The phthaloyl protecting group, however, cannot be used for the protection of the amino group in L-DOPA, since applicants have observed extensive racemization during the preparation of the phthaloyl-L-DOPA. Some C-terminal D, L-DOPA dipeptides have been reported by coupling D, L-DOPA-methyl ester and some simple N-Cbz amino acids. See, G. Losse, A. Barth and K. Jasche, *J. Prakt. Chem.*, 21, 32 (1963), and G. Losse, A. Barth and W. Langenbeck, *Chem. Ber.*, 95, 918 (1962), respectively.

The methyl ester could be hydrolyzed under $N_2$ after the N-Cbz group was cleaved. The phthalylglycyl-D, L-3,4-dihydroxyphenylalanine-methyl ester was also reported but the protective groups were not cleaved. See, J. J. O'Neill, F. P. Veitch and T. Wagner-Jauregg, *J. Org. Chem.*, 21, 363 (1956).

In one case, the preparation of beta-alanyl-L-3,4-dihydroxy-phenylalanine was reported. However, the way it was prepared, as well as the insufficient characterization of the dipeptide leads one to believe that it is unlikely that the compound was really obtained. See, C. Pinelli, M. Portelli, and M. Fioretti, *Farmaco (Ed. Sci.)*, 23, 859 (1968).

A. V. Bardoshian, et al, *Anal. Biochem.*, 49, 569 (1972) reported the use of L-leucyl-L-3,4-dihydroxyphenyl-alanine, which was used for the separation on TLC of the optical isomers of labeled DOPA.

In view of the above few literature data, applicants decided to use the N-formyl-diacetyl-L-DOPA for the preparation of the N-terminal dipeptide and diacetyl-L-DOPA-benzyl ester for the preparation of the C-terminal dipeptide. DCC (dicyclohexylcarbodiimide) was used as the coupling agent in all cases.

The N-formyl group can be cleaved by diluted HCl in alcohol, by catalytic hydrogenation or by oxidation with $H_2O_2$ and the benzyl esters, and the N-Cbz-groups can be removed by catalytic hydrogenation. See, G. Losse, and D. Nadolski, *J. Prakt. Chem.*, 24, 118 (1964), and G. Losse and W. Zonnchen, *Ann.*, 636,140 (1960).

PREPARATION OF THE COMPOUNDS OF CLASSES (VII) AND (VIII):

The compounds of class (VII) are prepared in a manner similar to that described for the preparation of the dipeptides of classes (V) and (VI). As the starting materials, we have on the one hand, 3,4-diacylated, N protected L-DOPA and on the other hand, we have the carboxy esters of 3,4-diacylated L-DOPA. Thus, N-formyl-3,4-diacetyloxy-L-phenylalanine was coupled with 3,4-diacetyloxy-L-phenylalanine-methyl ester. By treatment with methanolic HCl, the N formyl and acetyloxy groups were cleaved, thus obtaining 3,4-dihydroxy-L-phenylalanyl-methyl ester HCl. The free dipeptide was obtained by alkaline hydrolysis of the methyl ester in an inert atmosphere.

The corresponding bis-3,4-diacylated dipeptide was obtained by acylation of the free dipeptide, using the method described for the preparation of those compounds of class (I).

The compounds of class (VIII) are obtained, using general procedures as outlined in the literature [Greenstein and Winitz, *The Chemistry of Amino Acids and Peptides*, Volume 2 (1964), published by McGraw-Hill] with the proviso that the hydroxyl groups of the catechol system must be protected through acylation prior to preparing the polypeptide. Accordingly, 3,4-diacetyloxy-L-phenylalanoyl chloride HCl can be obtained by treatment of 3,4-diacetyloxy-L-phenylalanine with $PCl_5$ in acetyl chloride. The obtained chloride, after neutralization, undergoes coupling to form the corresponding acylated polypeptide.

The acetyl groups can be removed by alkaline or acidic hydrolysis to form the free polypeptide. This reaction scheme is carried out at standard pressure at about 0°C over a period of time of from 1 to 4 hours.

The compounds of the present invention are administered orally in the form of any oral, pharmaceutically acceptable dosage form (capsule, tablet, and the like). Generally speaking, the dosage amount of the compound administered, on a daily basis, will vary with the needs of the individual treated.

With the foregoing in mind, a better understanding of the present invention will be obtained from a review of the following examples, which are merely intended to be illustrative and non-limitative of the present invention.

EXAMPLE I (Preparation of 3,4-diacetyloxy-L-phenylalanine hydrochloride)

L-DOPA (19.72 g. 0.01 mole) is dissolved as its hydrochloride salt in 500 ml of glacial acetic acid by heating the same to approximately 100°C and adding HCl gas. The resulting clear solution is permitted to cool to 45°C and then 71 ml (5.5 g, 1.0 mole) of acetyl chloride is added slowly to the above described solution. The reaction mixture is stirred at room temperature for approximately 16.0 hours using a drying tube filled with calcium chloride to protect it from atmospheric moisture. The entire reaction mixture is then added to one liter of ether and stirred for 15 minutes and the resulting product is recovered by filtration.

The yield of final product was 28.5 g (90%). The melting point of the final product was 192°–193°C (uncorrected). The nuclear magnetic resonance spectrum (nmr) was consistent with the compound obtained. The Analysis Calculated for: $C_{13}H_{16}O_6NCl$ was: C, 49.14; H, 5.08; N, 4.41; and Cl, 11.16. Found: C, 48.98; H, 5.26; N, 4.17; and Cl, 11.25

EXAMPLE II (Preparation of the potassium salt of 3,4-diacetyloxy-N-[1-methyl-2-acetyl-vinyl]-L-phenylalanine)

3,4-diacetyloxy-L-phenylalanine hydrochloride (6.34 g, 0.002 mole) was dissolved with stirring in 20 ml of methanol in the presence of a nitrogen atmosphere. After 0.5 hours of stirring under nitrogen, 40 ml of 1N KOH in methanol was introduced and then, 2.30 ml (0.22 mole) of acetylacetone was added. The reaction mixture was stirred in the presence of nitrogen for 24 hours at room temperature and the precipitated KCl was then filtered off, together with some unreacted starting material. The filtrate was evaporated to dryness in vacuo. The product was thus obtained as an amorphous hygroscopic white powder in a yield of 7.08 g (88%). Analysis Calculated for: $C_{18}H_{20}NK \cdot H_2O$: C, 51,54; H, 5.29; N, 3.37. Found: C, 51.74; H, 5.38; and N, 3.81. The decomposition point on a differential scanning calorimeter (DSC) was 222°C. The nmr was consistent with the compound obtained.

EXAMPLE III (Preparation of 3,4-dihydroxy-L-phenylalanine-methyl ester hydrochloride and 3,4-diacetyloxy-L-phenylalanine-methyl ester hydrochloride).

First, 3,4-dihydroxy-L-phenylalanine-methyl ester hydrochloride was prepared. To obtain this compound, thionyl chloride (10.16 ml) was added, drop-wise to a cool (ice-bath) well-stirred absolute methanol (101.6 ml). To this solution, there was then added 23.02 g (0.117 mole) of 3,4-dihydroxy-L-phenylalanine, in portions, such that the temperature was maintained at 5°C. The solution was kept at 40°C for 2.5 hours and then, the solution was concentrated, in vacuo to dryness. Dry ether was added to the residue and the solution was cooled overnight to yield 28.67 g (m.p. 169°–172°C) of final product, a 99.3% yield. The nmr spectrum was consistent with the proposed structure for the compound obtained and analysis of the final compound obtained was as follows: Analysis Calculated for: $C_{10}H_{14}NO_4Cl$: C, 48.48; H, 5.70; and N, 5.66. Found: C, 47.95; H, 5.30; and N, 6.16.

In the next step, the obtained 3,4-dihydroxy-L-phenylalanine-methyl ester hydrochloride was then acylated in the following manner. A glacial acetic acid (661 ml) suspension containing 25.4 g (0.1 mole) of 3,4-dihydroxy-L-phenylalanine-methyl ester hydrochloride was warmed to 110°C and subsequently, hydrogen chloride was bubbled through the mixture for a period of 4 minutes. The solution was cooled to 45°C and acetyl chloride (101.3 ml) was then added. This solution was stirred at room temperature overnight and then, diluted with 1.5 liters of dry ether. White crystals began to precipitate immediately and subsequently, these crystals were filtered and dried over phosphorous pentoxide to yield 28.51 g (m.p. 181°–183°C, 83.7% yield) of the final product. The nmr spectrum was consistent with 3,4-diacetyloxy-L-phenylalanine-methyl ester hydrochloride. Upon analysis, the following data was obtained. Analysis Calculated for: $C_{14}H_{18}NO_4Cl$: C, 50.68; H, 5.47; N, 4.22; and Cl, 10.70. Found: C, 50.50; H, 5.21; and N, 4.67.

A sample of the obtained 3,4-diacetyloxy-L-phenylalanine-methyl ester hydrochloride was recrystallized from methanol-ether to yield the analytically pure compound. Found: C, 50.42; H, 5.61; N, 4.09; and Cl, 10.44.

In a similar manner described above, the compound 3,4-diacetyloxy-L-phenylalanine benzyl ester hydrochloride can be prepared and was prepared. Upon analysis, the following data was obtained. Analysis Calculated for: $C_{20}H_{22}O_6NCl$: C, 58.89; H, 5.44; N, 3.44; and Cl, 8.69. Found: C, 58.58; H, 5.48; N, 3.33; and Cl, 8.95.

EXAMPLE IV (Preparation of 3,4-dihydroxy-L-phenylalanine-benzyl ester hydrochloride)

3,4-dihydroxy-L-phenylalanine (15.0 g, 0.076 mole) was suspended in benzyl alcohol (381 ml). This suspension was then cooled with an ice bath to 5°C and then, the suspension was treated with thionyl chloride (76.2 ml). The resulting solution was heated to within a temperature range of from 95° to 100°C for 5.0 hours, in a nitrogen atmosphere and then, the suspension was cooled to room temperature and diluted with 1.5 liters of dry ether to yield a solid precipitate. The suspension was stirred at room temperature overnight, filtered, and then washed with ether and dried in a vacuum oven to yield 7.70 g (32% yield) of the desired benzyl ester hydrochloride having a m.p. of 171°–175°C, with shrinking at 165°C.

An oil had also formed in the bottom of the reaction flask overnight and this oil was dissolved in a minimal amount of methanol. A white solid was precipitated with ether, and the white solid was filtered and then dried in a vacuum oven to give 1.20 g (5% yield, m.p. 178°–181°C) of the benzyl ester hydrochloride. The nmr spectrum was consistent with the proposed structure of the compound isolated and upon analysis, the following data was obtained. Analysis Calculated for: $C_{16}H_{18}NO_4Cl$: C, 59.35; H, 5.60; and N, 4.33. Found: C, 59.47; H, 5.32; and N, 4.76. The nmr spectrum of the fraction was identical with that of the analytical sample.

EXAMPLE V (Preparation of glycyl-3,4-diacetloxy-L-phenylalanine hydrochloride)

First, carbobenzoxyglycyl-3,4-diacetyloxy-L-phenylalanine-benzyl ester was obtained in the manner which follows. Dichloromethane (100 ml) solution containing 0.95 g (9.4 millimole) of triethylamine was permitted to react with 3.64 g (8.92 millimole) of 3,4-diacetyloxy-L-phenylalanine-benzyl ester hydrochloride for 0.3 hours at room temperature. The solution was then concentrated in vacuo at room temperature to dryness. The residue obtained was filtered and washed with ether to give 1.54 g of triethylamine hydrochloride, contaminated with 3,4-diacetyloxy-L-phenylalanine-benzyl ester in various stages of deprotection. For instance, 3,4-dihydroxy-L-phenylalanine-benzyl ester was obtained quantitatively if a large excess of triethylamine was employed to neutralize the hydrochloride. The ether filtrate was concentrated in vacuo at room temperature. The resulting residue was analyzed by nmr and found to be consistent with the proposed structure, 3,4-diacetyloxy-L-phenylalanine-benzyl ester.

The residue was estimated to contain 8.15 millimole of 3,4-diacetyloxy-L-phenylalanine-benzyl ester. The residue was dissolved in dichloromethane (50 ml) and carbobenzoxylglycine (1.70 g, 8.16 millimole) and dicyclohexylcarbodiimide (1.68 g, 8.15 millimole) was added to the solution in the order given. A white precipitate of dicyclohexylurea (DCCU) began to form immediately. The following day, the suspension was filtered and the residue was washed with dichloromethane (50 ml) to yield 1.55 g (85% yield) of DCCU. The combined dichlormethane filtrates were washed with 10 ml each, of 1N hydrochloric acid and water and then, concentrated in vacuo at room temperature to give 4.6 g of an oily residue. The oily residue was chromatographed on silica gel (Mallinckrodt Silic ARCC-7) using ether as the eluent to give 2.70 g of a yellow oil (1 spot on TLC, Rf 0.63 on silica gel, acetone eluent) whose nmr spectrum was consistent with carbobenzoxyglycyl-3,4-diacetyloxy-L-phenylalaninebenzyl ester, but which contained some impurities from the ether eluent. The oil was dissolved in ether (100 ml) and diluted with heptane. The ether-heptane mixture was decanted from the oil which formed. The oil (2.00 g, 44% yield) give a nmr spectrum consistent with the carbobenzoxyglycyl-3,4-diacetyloxy-L-phenylalanine-benzyl ester. The oil would not crystallize and was therefore employed without further purification in the next reaction step.

In this step, glycyl-3,4-diacetyloxy-L-phenylalanine hydrochloride was obtained as follows. 2.48 g (4.4 millimole) of carbobenzoxyglycyl-3,4-diacetyloxy-L-phenylalanine-benzyl ester was dissolved in 120 ml of methanol with 5 ml of glacial acetic acid. Then, 0.5 g of 10% Pd/C (palladium on carbon) was wetted with water (5 ml) and washed into the solution with water (approximately 5 ml). The resulting suspension wash shaken in hydrogen (30 lbs) for 24 hours. The suspension was filtered and washed with methanol (100 ml) and the combined filtrates were concentrated in vacuo at room temperature. The residue was dissolved in 10 ml of glacial acetic acid, saturated with hydrogen chloride and then treated with 10 ml of acetyl chloride in a tightly stoppered flask overnight and subsequently, the solution was diluted to 125 ml with ether. After two hours, the ether was decanted and the gummy residue obtained was suspended in dry ether and left stirring overnight. Then, the suspension was quickly filtered and the residue was dried in vacuo at 60° C to yield 0.87 g (m.p. 95°–118°C) of the glycyl-3,4-diacetyloxy-L-phenylalanine hydrochloride. Analysis Calculated for: $C_{15}H_{19}N_2O_7Cl$: C, 48.06; H, 5.11; and N, 7.48. Found: C, 48.42; H, 5.38; and N, 7.30.

EXAMPLE VI (Preparation of glycyl-3,4-diacetyloxy-L-phenylalanine-methyl ester hydrochloride)

A dichloromethane solution (150 ml) of 3,4-diacetyloxy-L-phenylalaninemethyl ester hydrochloride (4.136 g, 13.0 millimole) was permitted to react with 1.35 g (13.3 millimole) of triethylamine. After 10 minutes, 2.718 g (13.0 millimole) of carbobenzyloxyglycine was added thereto, and then 2.808 g (13.6 millimole) of dicyclohexylcarbodiimide was added. After 2 hours, the solution was filtered to yield 2.62 g (m.p. 228°–230°C, 90% yield) of DCCU. The filtrate was extracted with 10 ml each of 1N HCl and water. The dichloromethane layer was dried over sodium and concentrated in vacuo at room temperature to give 16.5 g of a white solid (1 spot of TLC Silica gel, acetone, Rf 0.42). The white solid was dissolved in dichloromethane (60 ml) and the solution was then filtered and diluted to 220 ml with hexane. The following day, the solution was filtered and the residue was air dryed to give 5.5 g (m.p. 130°–131°C, 87% yield) of carbobenzyloxyglycyl-3,4-diacetyloxy-L-phenylalanine-methyl ester. The mother liquor was concentrated (45 ml) to give 233 mg. (m.p. 129°–130°C, 3% yield) more of the aforementioned ester. The nmr spectrum was consistent with the proposed structure of the compound isolated.

Upon analysis, the following data was obtained. Analysis Calculated for: $C_{24}H_{26}N_2O_9$: C, 59.25; H, 5.39; and N, 5.76. Found: C, 59.54; H, 5.39; and N, 5.74.

Next, 3.00 g (6.17 millimole) of the above isolated ester was dissolved in methanol (100 ml) and glacial acetic acid (5 ml). The solution was then shaken in a Parr apparatus for 16 hours over 10% Pd/C (0.4 g) under a hydrogen atmosphere (35 lbs). The solution was then filtered and concentrated in vacuo at room temperature. The residue obtained was dissolved in 10 ml of glacial acetic acid, saturated with hydrogen chloride and treated with 10 ml of acetyl chloride. The solution was stirred at room temperature overnight in a tightly sealed reaction flask and then diluted to 125 ml with ether to give a light brown gum. The ether was decanted and the residue was suspended in anhydrous ether (100 ml). The suspended solid was dispersed with a spatula and allowed to stir until it became homogeneous. It was then filtered and the residue was dried in a vacuum oven at 60°C to yield 0.58 g (m.p. 80°–100°C, 24% yield) of glycyl- 3,4-diacetyloxy-L-phenylalanine-methyl ester hydrochloride from carbobenzyloxyglycyl-3,4-diacetyloxy-L-phenylalanine-methyl ester. The nmr spectrum was consistent with the proposed structure of the compound obtained and upon analysis of the compound, the following data was obtained. Analysis Calculated for: $C_{16}H_{21}O_7N_2Cl$: C, 49.42; H, 5.44; and N, 7.21. Found: C, 49.65; H, 5.50; and N, 7.47.

EXAMPLE VIII (Preparation of 3,4-diacetyloxy-L-phenylalanyl-glycine hydrochloride)

First, it was necessary to prepare 3,4-diacetyloxy-L-phenylalanine-N-formate. This product was obtained in the manner described below.

3,4-diacetyloxy-L-phenylalanine hydrochloride (15.00 g. 47.2 millimole) was dissolved in 20 ml of methanol and diluted to 900 ml with dichloromethane. To this solution, there was added, with vigorous stirring, 4.80 g (47.5 millimole) of triethylamine, which caused a gelatinous mass to form. After one hour, this mass was filtered and the residue was suspended in dichloromethane (300 ml) and filtered again. The residue was still contaminated with triethylamine hydrochloride. Consequently, it was suspended in dichloromethane (300 ml) again, and stirred for 3.5 hours. The suspension was filtered and dried at room temperature in vacuo to yield 12.5 g (95% yield by nmr) of 3,4-diacetyloxy-L-phenylalanine.

Next, 12.5 g (44.6 millimole) of the isolated 3,4-diacetyloxy-L-phenylalanine was dissolved in 35 ml of 98% formic acid and cooled with an ice bath at 5°C. Acetic anhydride (9.6 g, 94.1 millimoles) was added, drop-wise to the cool, well-stirred solution in such a manner that the treatment remained at 5°C. After 3 hours, the solution was concentrated in vacuo at room temperature and the residue was dissolved in acetone (200 ml). This process was repeated twice and the residue was recrystallized from acetone, (750 ml) to yield 4.95 g (m.p. 135°–137°C) of 3,4-diacetyloxy-L-phenylalanine-N-formate. The mother liquor was concentrated on a hot plate to 40 ml and then cooled to yield 3.50 g (m.p. 130°–135°C) of 3,4-diacetyloxy-L-phenylalanine-N-formate. The mother liquor was again concentrated to yield 1.75 g (m.p. 123°–133°C) of the aforementioned compound, after which the solution was diluted with 200 ml of ether to yield 1.53 g (m.p. 112°–120°C) of 3,4-diacetyloxy-L-phenylalanine-N-formate. All fractions had the same TLC (Rf 0.5 silica gel, acetone). The last two fractions were combined and recrystallized from acetone (20 ml) to yield 1.50 g (m.p. 130°–135°C) of 3,4-diacetyloxy-L-phenylalanine-N-formate for a 69% yield (9.95 g) of the pure compound. The nmr spectrum was consistent with the proposed structure of the compound obtained.

Next, N-formyl-3,4-diacetyloxy-L-phenylalanyl-glycine-benzyl ester was prepared. To obtain this compound, the 3,4-diacetyloxy-L-phenylalanine-N-formate, obtained earlier (4.015 g, 13.00 millimole) was added to a dichloromethane (200 ml) solution containing triethylamne (1.35 g, 13.3 millimole) and glycine benzyl ester p-toluenesulfonate (4.40 g, 13.06 millimole). The resulting suspension was vigorously shaken until all of the 3,4-diacetyloxy-L-phenylalanine-N-formate was in solution. Then, 2.80 g (13.6 millimole) of dicyclohexylcarbodiimide was added. After 4.5 hours, the reaction was filtered and the residue (2.41 g, m.p. 206°–210°C, 83% yield) of DCCU was discarded. The filtrate was extracted with 10 ml each of water and 1N HCl. The dichloromethane solution was then dried over sodium sulfate and concentrated in vacuo at room temperature. The residue was chromatographed on silica gel (Silic ARCC-7) using acetone-ether (20:80 to 40:60) as the eluent to give 2.33 g (39% yield) of N- formyl-3,4-diacetyloxy-L-phenylalanyl-glycine-benzyl ester (m.p. 120.5°–120°C). The nmr spectrum was consistent with the proposed structure of the compound isolated. Upon analysis the following data was obtained. Analysis Calculated for: $C_{23}H_{24}N_2O_8$: C, 60.52; H, 5.29; and N, 6.14. Found: C, 60.25; H, 5.10; and N, 6.01.

Next, the step of deprotecting the N-formyl-3,4-diacetyloxy-L-phenylalanylglycine-benzyl ester was performed. 0.90 g (2.0 millimole) of the aforementioned compound was allowed to react with a 2.2 ml of a 1N methanolic-hydrochloric acid solution (prepared by diluting 2 ml of concentrated hydrochloric acid to 24 ml with methanol) overnight. Initially, a suspension formed and an additional 5 ml of methanol was added to the suspension. After about 0.5 hours, all of the solid had gone into solution. The solution was concentrated in vacuo at room temperature and the nmr spectrum of the residue showed the absence of $CH_3CO_2$ and O=CH-N absorptions. The residue was dissolved in 60 ml of anhydrous methanol to which 0.5 ml of glacial acetic acid had been added. The solution was shaken in a Parr shaker under hydrogen atmosphere over 0.1 g of a 10% Pd/C catalyst overnight. The suspension was then filtered to remove the catalyst and concentrated in vacuo at room temperature. The residue was twice diluted with acetone (100 ml) and concentrated. Then, it was dissolved in glacial acetic acid saturated with hydrogen chloride (10 ml) and allowed to react with acetyl chloride (10 ml). A solid formed, but soon went back into solution. After eight hours at room temperature, the acetic acid solution was then diluted to 125 ml with ether. The ether was then decanted and the gummy dark residue left behind was suspended in ether (100 ml). The suspension was stirred overnight to yield a fine white solid in suspension, which was filtered quickly and dried in a vacuum dessicator to yield 0.59 g (shrinking at 100°C, wet at 114°C, a foaming from 120°–127°C, 78% yield) of 3,4-diacetyloxy-1-phenylalanyl-glycine hydrochloride. The nmr was consistent with the proposed structure of the compound obtained and upon analysis of a sample of this compound, by recrystallization from methanol-ether, the following data was obtained. Analysis Calculated for: $C_{15}H_{19}N_2O_7Cl$: C, 48.06; H, 5.11; and N, 7.48. Found: C, 48.22; H, 5.34; and N, 7.72.

IN VIVO COMPARISON OF L-DOPA PER SE VERSUS SELECTIVE L-DOPA DERIVATIVES OF THE PRESENT INVENTION

In Table I, reproduced on the following page, values are shown relative to the blood concentration of L-DOPA per se and selected L-DOPA derivatives of the present invention, following oral administration of 0.1 g of L-DOPA and an equivalent amount of an L-DOPA derivative of this invention to Beagle dogs.

Respective of Table I, the following information is pertinent:

-Reference to (a) refers to the values obtained from three Beagle dogs for each compound tested, the Beagle dogs being of both sexes and weighing from 12 to 14 Kg.

Reference to [L-DOPA] refers to the concentration of L-DOPA.

compound (o) is L-DOPA per se.

Compound (I) is 3,4-diacetyloxy-L-phenylalanine hydrochloride.

Compound (II) is the potassium salt of 3,4-diacetyloxy-N-[1-methyl-2-acetylvinyl]-L-phenylalanine.

Compound (III) is 3,4-dihydroxy-L-phenylalanine-methyl ester, HCl.

Compound (IV) is 3,4-diacetyloxy-L-phenylalanine-methyl ester, HCl.

Compound (V) is 3,4-dihydroxy-L-phenylalanine-benzyl ester hydrochloride.

Compound (VI) is 3,4-diacetyloxy-L-phenylalanine-benzyl ester hydrochloride.

Compound (VII) is glycyl-3,4-diacetyloxy-L-phenylalanine-hydrochloride.

Compound (VIII) is glycyl-3,4-diacetyloxy-L-phenylalanine-methyl ester hydrochloride.

Compound (IX) is 3,4-diacetyloxy-L-phenylalanyl-glycine hydrochloride.

The blood level data provided above in Table I was obtained according to the published procedures set forth in Items (I) through (IX).

(1) H. E. Spiegel and A. C. Tonchen, *Clinical Chemistry*, Volume 16, No. 9 (1970).

(2) T. L. Sourkes and G. S. Murphy, *Methods Med. Res.*, 9, 147 (1961).

(3) H. Takashi and T. B. Fitzpatrick, *J. Invest, Dermatol.*, 41, 161 (1964).

(4) A. Carlson and D. Waldeck, *A.C.T.A. Physiol, Scandinav.*, 44, 293 (1958).

(5) A. H. Anton and D. F. Sayre, *J. Pharmacol.*, 145, 326 (1964).

(6) R. Bruce, *Anal. Chem.*, 41, 977 (1969).

(7) E. Anggard, Ibid, 41, 1250 (1969).

(8) E. Anggard, *A.C.T.A. Chim. Scand.*, 23, 3110 (1969)

(9) S. T-ahn, A. L. Prasad, R. Eelesie, *Analyt. Biochemistry*, 46, 557 (1972).

The above results clearly demonstrate that the L-DOPA pro-drug forms of this invention permit L-DOPA to be released in the blood stream at higher blood levels than that level achieved with L-DOPA per se. This indicates that the various pro-drugs studied, provide efficient protection of the L-DOPA molecule against extensive metabolism prior and/or during the

TABLE I

| Compound No. | [L-DOPA] (µg/ml) at time (hours)[a] | | | | | | | µg/hr/ml area under the curve | µg./ml L-DOPA at the peak | hours time for reaching the peak |
|---|---|---|---|---|---|---|---|---|---|---|
| | 0.5 | 1 | 1.5 | 2 | 3 | 4 | 6 | | | |
| O | 0.14 | 0.64 | — | 0.87 | — | 0.22 | 0.11 | 2.6 | 0.9 | 1.8 |
| I | 1.57 | 1.75 | 1.38 | 1.10 | 0.35 | 0.13 | 0.06 | 7.20 | 1.8 | 0.8 |
| II | 2.16 | 2.29 | 1.61 | 0.70 | 0.40 | 0.28 | 0.20 | 9.07 | 2.4 | 0.9 |
| III | 1.33 | 0.18 | 0.60 | 0.39 | 0.26 | 0.12 | 0.05 | 4.60 | 1.6 | 0.8 |
| IV | 0.06 | 1.13 | 1.11 | 0.39 | 0.12 | 0.09 | 0.02 | 3.56 | 1.6 | 1.2 |
| V | 2.30 | 1.03 | 0.55 | 0.31 | 0.14 | 0.14 | 0.06 | 5.94 | 2.2 | 0.8 |
| VI | 1.71 | 1.30 | 1.08 | 0.55 | 0.20 | 0.14 | 0.05 | 5.96 | 2.3 | 0.5 |
| VII | 1.34 | 1.95 | 1.21 | 0.43 | 0.27 | 0.13 | 0.02 | 7.25 | 2.4 | 0.75 |
| VIII | 0.79 | 1.17 | 0.51 | 0.33 | 0.08 | 0.02 | 0 | 3.38 | 1.7 | 0.80 |
| IX | 0.26 | 1.30 | 1.62 | 0.80 | 0.23 | 0.03 | 0 | 5.30 | 1.8 | 1.2 | absorption process. Moreover, the above studies demonstrate that pro-drugs were converted back to L-DOPA in accordance with the "pro-drug" definition provided at the outset of this application.

The pro-drug forms of this invention are suitably administered in oral dosage form, such as by tablet or capsule, by comining the same in a therapeutic amount with any oral pharmaceutically acceptable inert carrier, such as lactose, starch (pharmaceutical grade), dicalcium phosphate, calcium sulfate, kaolin, mannitol, and powdered sugar. In addition, when required, suitable binders, lubricants, disintegrating agents, and coloring agents can also be added to the oral dosage form. Typical binders include starch, gelatin, sugars, such as sucrose, molasses, and lactose, natural and synthetic gums, such as acacia, sodium alginate, extract of Irish moss, carboxymethylcellulose, methyl cellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include without limitation, starch, methylcellulose, agar, bentonite, cellulose and wood products, alginic acid, guar gum, citrus pulp, carboxymethylcellulose, and sodium lauryl sulfate. If desired, a conventionally pharmaceutically acceptable dye can be incorporated into the dosage unit form.

Any skilled artisan can prepare these oral dosage forms by simply referring to the oral dosage form preparatory procedure outlined in *Remington's Practice of Pharmacy*, Fourteenth Edition, (1970), pages 1659 through 1698, inclusive.

While the therapeutic dosage range for the compounds of this invention will vary with the needs of the individual, generally speaking therapeusis on a daily basis is achieved with about ⅓ the amount of the L-DOPA therapeutic dosage administered at present. In certain cases, therapeusis is achied with less than ⅓ the amount of the normal L-DOPA therapeutic dosage amount. These dosage guidelines are independent of the patient's size and/or weight.

As an example, an adult human male, suffering from Parkinson's Disease can be successfully treated by administering, on a daily basis, about 2.0 grams of the L-DOPA pro-drug form of Compound VII described at page 30 (glycyl-3,4-diacetyloxy-L-phenylalaninehydrochloride).

Although the present invention has been adequately described in the foregoing specification and examples included therein, it is obviously apparent that various changes and/or modifications can be made thereto by the skilled artisan without departing from the spirit and scope thereof.

What we claim is:

1. A method for treating Parkinson's Disease in warmblooded animals which comprises administering thereto, an antiParkinsonism effective amount of a compound having the formula:

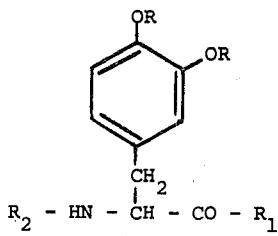

wherein R represents a member selected from the group consisting of hydrogen, $-COCH_3$, $-COC_2H_5$, $-COOC_2H_5$, and $-CO-C(CH_3)_3$; wherein $R_1$ represents a member selected from the group consisting of hydroxyl and $-OM$, wherein M represents a member selected from the group consisting of an alkali metal and an ammonium ion; and wherein $R_2$ represents $-(R_5)CO-CH=C(R_4)-$, wherein $R_4$ represents methyl or ethoxy, and wherein $R_5$ represents a member selected from the group consisting of methyl, $-C_6H_5$, and $-OC_2H_5$.

2. The method of claim 1, wherein said compound is administered in combination with a pharmaceutically acceptable inert carrier material.

3. The method of claim 1, wherein said compound is 3,4-diacetyloxy-N[1-methyl-2-acetylvinyl]-L-phenylalanine and its alkali metal salt.

4. The method of claim 1, wherein said compound is 3,4-dihydroxy-N[1-methyl-2-acetylvinyl]-L-phenylalanine and its M salt, wherein M represents an alkali metal.

5. The method of claim 1, wherein said compound is 3,4-dipivalyloxy-N[1-methyl-2-acetylvinyl]-L-phenylalanine and its M salt, wherein M represents an alkali metal.

6. The method of claim 1, wherein said compound is 3,4-dihydroxy-N[1-ethoxy-2-acetylvinyl]-L-phenylalanine and its M salt, wherein M represents an alkali metal.

7. The method of claim 1, wherein said compound is 3,4-diacetyloxy-N[1-ethoxy-2-acetylvinyl]-L-phenylalanine and its M salt, wherein M represents an alkali metal.

8. The method of claim 1, wherein said compound is 3,4-dipivalyloxy-N[1-ethoxy-2-acetylvinyl]-L-phenylalanine and its M salt, wherein M represents an alkali metal.

9. A pharmaceutical composition for use in the treatment of Parkinson's Disease, comprising a pharmaceutically acceptable inert carrier material in combination with an anti-Parkinsonism effective amount of a compound having the formula:

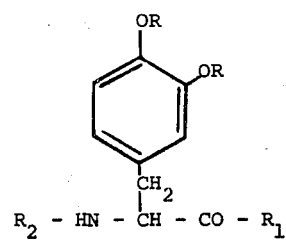

wherein R represents a member selected from the group consisting of hydrogen, $-COCH_3$, $-COC_2H_5$, $-COOC_2H_5$, and $-CO-C(CH_3)_3$; wherein $R_1$ represents a member selected from the group consisting of hydroxyl and $-OM$, wherein M represents a member selected from the group consisting of an alkali metal and an ammonium ion; and wherein $R_2$ represents $-(R_5)CO-CH=C(R_4)-$, wherein $R_4$ represents methyl or ethoxy, and wherein $R_5$ represents a member selected from the group consisting of methyl, $-C_6H_5$, and $-OC_2H_5$.

10. The composition of claim 9, wherein said compound is 3,4-diacetyloxy-N[1-methyl-2-acetylvinyl]-L-phenylalanine and its alkali metal salt.

11. The composition of claim 9, wherein said compound is 3,4-dihydroxy-N[1-methyl-2-acetylvinyl]-L- phenylalanine and its M salt, wherein M represents an alkali metal.

12. The composition of claim 9, wherein said compound is 3,4-dipivalyloxy-N[1-methyl-2-acetylvinyl]-L-phenylalanine and its M salt, wherein M represents an alkali metal.

13. The composition of claim 9, wherein said compound is 3,4-dihydroxy-N[1-ethoxy-2-acetylvinyl]-L-phenylalanine and its M salt, wherein M represents an alkali metal.

14. The composition of claim 9, wherein said compound is 3,4-diacetyloxy-N[1-ethoxy-2-acetylvinyl]-L-phenylalanine and its M salt, wherein M represents an alkali metal.

15. The composition of claim 9, wherein said compound is 3,4-dipivalyloxy-N[1-ethoxy-2-acetylvinyl]-L-phenylalanine and its M salt, wherein M represents an alkali metal.

* * * * *